US00RE43793E

(19) United States
(12) Reissued Patent
Descouts et al.

(10) Patent Number: US RE43,793 E
(45) Date of Reissued Patent: Nov. 6, 2012

(54) ENDOSSEOUS IMPLANT

(75) Inventors: Pierre Descouts, Neydens (FR); Bjorn-Owe Aronsson, Veyrier (CH); Michael Gratzel, St. Sulpice (CH); Carine Viorney, Carantec (FR); Peter Pechy, Lausanne (CH)

(73) Assignees: Universite de Geneve, Geneva (CH); Ecole Polytechnique Federale de Lausanne, Lausanne (CH)

(21) Appl. No.: 13/213,472

(22) Filed: Aug. 19, 2011

Related U.S. Patent Documents

Reissue of:
(64) Patent No.: 7,727,540
Issued: Jun. 1, 2010
Appl. No.: 10/432,026
PCT Filed: Nov. 19, 2001
PCT No.: PCT/EP01/13364
§ 371 (c)(1),
(2), (4) Date: Aug. 28, 2003
PCT Pub. No.: WO02/40074
PCT Pub. Date: May 23, 2002

(30) Foreign Application Priority Data

Nov. 20, 2000 (WO) ..... PCT/EP00/11510

(51) Int. Cl.
*A61C 8/00* (2006.01)
*A61F 2/28* (2006.01)

(52) U.S. Cl. ..... 424/422; 623/23.57; 433/201.1; 606/76

(58) Field of Classification Search ..... None
See application file for complete search history.

(56) References Cited

U.S. PATENT DOCUMENTS

| | | | |
|---|---|---|---|
| 4,330,537 | A | 5/1982 | Francis |
| 4,712,681 | A | 12/1987 | Branemark et al. |
| 5,324,519 | A | 6/1994 | Dunn et al. |
| 5,646,134 | A | 7/1997 | Yates |
| 5,733,564 | A | 3/1998 | Lehtinen et al. |
| 5,824,651 | A | 10/1998 | Nanci et al. |
| 7,090,496 | B2 | 8/2006 | Descouts et al. |

FOREIGN PATENT DOCUMENTS

| | | |
|---|---|---|
| EP | 0 860 213 | 8/1998 |
| WO | 92 09697 | 6/1992 |
| WO | 97/14716 | 4/1997 |
| WO | 98/52619 | 11/1998 |
| WO | 99 11202 | 3/1999 |
| WO | 99/31126 | 6/1999 |
| WO | 02/13872 | 2/2002 |
| WO | 02/14350 | 2/2002 |

OTHER PUBLICATIONS

Carine Viornery, "Surface functionalization of titanium with phosphonated ligands to improve bone bonding", Thése No. 2309, Lausanne, EPFL, 2000.

Abstract of A. Sewing et al., "Cell Culture Study on Biomimetic Coatings and Adhesion Peptides as Functionalized Coating for Dental Implants", Conference at 16th European Conference on Biomaterials, Sep. 12-14, 2001, London, UK.

Abstract of S. Röβler et al., "Biomimetic Coatings Functionalized with Adhesion Peptides for Dental Implants", Conference at 16th European Conference on Biomaterials, Sep. 12-14, 2001, London, UK.

Thesis of Martin Kantlehner, Techincal University of Munich, 2000.

*Primary Examiner* — Robert A Wax
*Assistant Examiner* — Danah Al-Awadi
(74) *Attorney, Agent, or Firm* — Wenderoth, Lind & Ponack, L.L.P.

(57) ABSTRACT

Endosseous implant to be applied to a human or animal bone, wherein the surface of the implant is made from titanium or a titanium alloy, said implant having a smooth or rough surface texture, which is characterized in that said surface has been treated with at least one selected organic phosphonate compound or a pharmaceutically acceptable salt or ester or an amide thereof; process for producing said implants.

38 Claims, No Drawings

ENDOSSEOUS IMPLANT

Matter enclosed in heavy brackets [ ] appears in the original patent but forms no part of this reissue specification; matter printed in italics indicates the additions made by reissue.

*This application is a reissue application of U.S. application Ser. No. 10/432,026, filed Aug. 28, 2003, which issued as U.S. Pat. No. 7,727,540, issued Jun. 1, 2010, which is a national stage application of International Application No. PCT/EP01/13364, filed Nov. 19, 2001, which claims priority to International Application No. PCT/EP00/11510, filed Nov. 20, 2000.*

The present invention relates to a metallic endosseous implant made from titanium or a titanium alloy to be applied to a human or animal bone, said implant having a smooth or rough surface texture, and wherein said surface has been treated with at least one selected organic compound carrying one or more phosphonic acid group [—$P(O)(OH)_2$] or a derivative thereof, preferably as a pharmaceutically acceptable salt or ester or amide thereof. It has been shown that such chemically modified surface surprisingly enhances the bone bonding strength. Implants according to the present invention may be used as prostheses in medicine, more specifically in orthopaedics, for replacing or strengthening broken or diseased bones, and in dentistry, for anchoring artificial teeth and for anchoring of bone anchored hearing prosthesis.

Implants which are used as prostheses in medicine for replacing or strengthening broken or diseased bones or as artificial teeth are known. These implants must be made of a non-corrosive material and must be compatible with the surrounding tissue without producing immunologic reactions effecting rejection by the body. In the following. the terms "surface" or "contact surface" refer to the titanium or a titanium alloy implant surface not yet treated according to the present invention and the term "modified surface" to the surface treated according to the present invention.

It is known that to implant devices in the form of screws, plates, nails, pins, and specially formed parts into the skeletal structure of humans and animals as artificial prosthetic is a means for permanent replacement of missing structural parts or as permanent anchoring devices. An excellent "osseointegration " is required for those situations where the implanted device should remain permanently adhered to the contacting bone surface.

It is generally known to use titanium metal or titanium alloys for such implants. When carefully produced, the titanium implant with its surface oxide exhibits biocompatibility in the sense that it remains passive for bone regeneration and does not per se induce adverse reactions such as inflammation or soft tissue generation or encapsulation. The interface obtained between the implant and the bone tissue normally consists of a protein layer of about 100 nm to 1 μm thickness preventing the bone tissue from being in direct molecular contact with the implant.

The actual state of the art for endosseous implants is based on different approaches, for example (i) the creation of a suitable roughness of the implant surface giving a mechanical interlocking between bone and implant and/or (ii) coating the titanium or titanium alloy surface of the implant, e.g. with an artificial hydroxyapatite for improving the healing process and the bone-implant intimate contact.

It is known that a high surface roughness on titanium implants increases the mechanical stability of the implant in the bone tissue. Mechanical surface treatment significantly alters the topography, while the surface chemistry remains substantially unchanged. The disadvantages of an implant with a high surface roughness are that a purely mechanical anchoring is very sensible to micromotions which may lead to a deterioration of the mechanical anchorage and that the osseointegration time of the implant is relatively long.

Coating the surface of the implant with an artificial hydroxyapatite decreases the osseointegration time. However, it is very difficult, if not impossible, to produce hydroxyapatite coatings with a long term stability on load bearing implants. The interface between the coating and the implant is often disrupted or the coatings are flaked off.

U.S. Pat. No. 5,733,564 suggests to use selected bisphosphonates which are known drug substances for the promotion of bone tissue formation by coating titanium metal surfaces of prostheses or implants with these compounds.

It has now been found that if the surface of a titanium or a titanium alloy endosseous implant has been treated with at least one selected organic compound as defined herein below carrying one or more phosphonic acid groups or a derivative thereof, preferably an ester, an amide or a salt thereof, as defined herein below, said surface shows a surprisingly improved bone bonding strength and a surprisingly shortened osseointegration time compared to the non treated surface and does not have the disadvantages as known for surfaces having a hydroxyapatite coating.

The present invention is defined in the claims. The present invention specifically refers to an endosseous implant to be applied to a human or animal bone, wherein the surface of the implant is made from titanium or a titanium alloy, said implant having a smooth or rough surface texture, which is characterized in that said surface has been treated with at least one organic compound corresponding to the general formula (I):

$$A\text{-}[P(O)(OH)_2]_p \qquad (I),$$

or a pharmaceutically acceptable derivative thereof, which is preferably an ester, an amide or a salt thereof, wherein A means $A_1$ or $A_2$, and $A_1$ is a residue of a linear, branched or cyclic, saturated or unsaturated, hydrocarbon residue with n carbon atoms, whereby said residue may be substituted by hydroxyl and/or carboxyl and optionally further interrupted by one or more oxygen and/or sulphur and/or nitrogen atoms, carrying p phosphonic acid groups, wherein n is a number from 1 to 70, preferably 1 to 40, preferably 1 to 22, and when n is 1 and p is 2: A is —$CH_2$—, or when n is 1: p is 3 or 4, preferably 3, or when n is 2 to 10: p is 2, provided each phosphonic acid group or phosphonic acid ester group is bound to a different carbon atom within the same molecule; or when n is 2 to 10: p is 3, 4, 5 or 6, preferably 3, 4 or 5, preferably 3 or 4; or when n is 11 to 70: p is 2, 3, 4, 5 or 6, preferably 2, 3, 4 or 5, preferably 2, 3 or 4;

or A means $A_2$ and $A_2$ is a residue of an amino acid or of a sequence of amino acids resp. of a protein or of a polypeptide, preferably a residue of the superfamily of Transforming Growth Factor beta (TGF-β); or a residue of a specific drug molecule, wherein each residue $A_2$ carries p phosphonic acid groups, and p is 1 to 6, preferably 1, 2, 3 or 4, preferably 1, 2, or 3, when $A_2$ is a residue of an amino acid or of a sequence. of amino acids resp. of a protein or of a polypeptide; or p is 1 or 3-6, preferably 1, when $A_2$ is a residue of a specific drug molecule originally not bearing any phosphonic group, optionally falling under the definition given for $A_1$.

The present invention further refers to a process for producing the implant according to the present invention which is characterized in that said surface is treated with at least one organic compound of formula (I) or a derivative thereof, which is preferably an ester, an amide or a salt thereof.

It is assumed that the phosphonate compounds as specified herein, especially as acids or salts, form a covalent bond with the surface of the implant thereby improving the osseointegration properties of said surface to a remarkable and unexpected extent. The present invention however is not bound to this explanation.

$A_1$ preferably is a saturated hydrocarbon residue of the formula —($C_nH_{2n+2-p}$)—, wherein n means 1 to 70, preferably 1 to 40, preferably 1-22. Preferred is the free acid or the salt form of the compound of formula (I), preferably where the pharmaceutically acceptable salt is an alkali salt, preferably of sodium or potassium salt. If the pharmaceutically acceptable ester is used, the isopropyl phosphonate or ethyl phosphonate esters are preferred, examples of such esters are: tetra isopropyl methylenediphosphonate, hexaethyl ethane-1,1,2-triphosphonate, hexaisopropyl butane-1,1,4-triphosphonate, hexaisopropyl pentane-1,1,5-triphosphonate, hexaisopropyl pentane-2,2,5-triphosphonate, hexaisopropyl hexane-2,2,6-triphosphonate, octaisopropyl propane-1,1,3,3-tetraphosphonate, octaisopropyl heptane-1,4,4,7-tetraphosphonate, octaisopropyl nonane-1,5,5,9-tetraphosphonate.

The metallic surface of the endosseous implant to be treated according to the present invention may be made from titanium or a titanium alloy as known to be used for the production of endosseous implants. Titanium alloys may be made from titanium and any other metal known to form an alloy with titanium, such as chromium, niobium, tantalum, vanadium, zirconium, aluminium, cobalt, nickel and/or stainless steels. Such titanium metal alloys for making implants are known per se and are described for example in Breme et al., Metals as Biomaterials, pp. 1-71 (1998) the contents of which are incorporated herein by reference.

Implants according to the present invention may be in the form of screws, plates, nails, pins, and specially formed parts and may be used as prostheses in medicine, more specifically in orthopaedics, for replacing or strengthening broken or diseased bones, and in dentistry, for anchoring artificial teeth and for anchoring of bone anchored hearing prosthesis into the skeletal structure of humans and animals. The surface area of the implant which is to be bound to the body tissue resp. bones, may have a smooth or rough surface texture. Such surface textures are known and can be obtained for example by treating the surface mechanically and/or with acids and/or electrolytically and/or with a glow-discharge plasma and/or plasma spraying and/or or by electro machining. Such materials and processes have been described in different publications, for example in B. -O. Aronsson et al., J. Biomed. Mater. Res. 35 (1997), pp. 49f., the contents of which are incorporated herein by reference.

Examples of compounds of formula (I) wherein A is a residue of a saturated hydrocarbon are polyphosphonic acids such as methylenediphosphonic acid, ethane-1,2-diphosphonic acid, propane-1,3-diphosphonic acid, propane-1,3-diphosphonic acid, ethane-1,1,2-triphosphonic acid, butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid, heptane-1,4,4,7-tetraphosphonic acid, propane-1,1,3,3-tetraphosphonic acid, or nonane-1,5,5,9-tetraphosphonic acid.

Examples of compounds of formula (I) wherein A is a residue of a protein resp. polypeptide in the form of a Transforming Growth Factor beta (TGF-β) in which are included the all members of the superfamily of growth factors and particularly the TGF-β1, TGF-β2, TGF-β3, TGF-β4, and TGF-β5 as described for example in A. B. Roberts, M. B. Sporn, Handbook of Experimental Pharmacology, 95 (1990) pp. 419-472 or D. M. Kingsley, Genes and Development 8 (1994) p. 133-146, and references therein, where the peptide chain has been modified to contain an alkylphosphonic acid group or a derivative thereof, which is preferably an ester, an amide or a salt thereof. In this sense the compound of formula (I) represents a Transforming Growth Factor beta (TGF-β) as defined by the members of the superfamily of growth factors, preferably the TGF-β1, TGF-β2, TGF-β3, TGF-β4, and TGF-β5, wherein each time the peptide chain has been modified to contain at least one alkylphosphonic acid group or a derivative thereof, which is preferably an ester, an amide or a salt thereof.

Examples of compounds of formula (I) wherein A is a residue of a Bone Morphogenic Protein (BMP) (being a subfamily to the TGF family) e.g., the BMP-2 (BMP-2a), BMP-3, BMP-4 (BMP-2b), BMP-5, BMP-6, BMP-7 (OP-1), BMP-8 (OP-2), BMP-9, BMP-10, BMP-11, BMP-12, BMP-13, as found for example in J. M. Wozney et. al., Science 242 (1988) 1528-1534; A. J. Celeste et al., Proc. Natl. Acad. Sci. USA 87 (1990) 9843-9847; E. Özkaynak et al., J. Biol. Chem. 267 (1992) 25220-25227; Takao et al., Biochem. Biophys. Res. Com. 219 (1996) 656-662; WO 93/00432; WO 94/26893; WO 94/26892; WO 95/16035 and references therein, where the peptide chain has been modified to contain an alkylphosphonic acid group or a derivative thereof, which is preferably an ester, an amide or a salt thereof. These compounds are incorporated herein by reference. In this sense the compound of formula (I) represents a Bone Morphogenic Protein (BMP), preferably the BMP-2 (BMP-2a), BMP-3, BMP-4 (BMP-2b), BMP-5, BMP-6, BMP-7 (OP-1), BMP-8 (OP-2), BMP-9, BMP-10, BMP-11, BMP-12, BMP-13, wherein the peptide chain has been modified to contain at least one alkylphosphonic acid group or a derivative thereof, which is preferably an ester, an amide or a salt thereof.

Examples of compounds of formula (I) wherein A is a residue of an amino acid are 2-amino-4,4-bis-(diethoxyphosphoryl)-butyric acid as described for example in O. Fabulet et al., Phosphorus, Sulphur Silicon and Related Elements, 101, 225-234 (1995); 2-amino-5-(diethoxyphosphoryl)-pentanoic acid as described for example in I. G. Andronova et al., Russ. J. Gen. Chem. 66, 1068-1071 (1996); 2-amino-4-phosphonobutyric acid as described for example in X. Y. Jiao et al., Synth. Commun. 22, 1179-1186 (1992) and references therein. Further examples are all the principal twenty amino acids as described for example in L. Stryer, Biochemistry, 3rd edition (1988), pp. 17-22, where the amino acid is modified in an analogous way with an alkylphosphonic acid group or a derivative thereof, which is preferably an ester, an amide or a salt thereof, preferably wherein the compound of formula (I) is one of the principal twenty amino acids, preferably arginine, glycine, aspartic acid, alanine, valine, proline, serine, threonine, cysteine or lysine, wherein the amino acid has been modified to contain at least one alkylphossphonic acid group or a derivative thereof, said derivative being preferably an ester, an amide or a salt thereof. These compounds are incorporated herein by reference.

Examples of compounds of formula (I) wherein A is a residue of a peptide comprise but are not limited to RGD-containing peptides, RGDS-peptides, GRGDS-peptides, RGDV-peptides, RGDE-peptides, and/or RGDT-peptides. Such peptides are described for example in Y. Hirano, J. Biomed. Materials Res., 25 (1991), pp. 1523-1534 or in WO 98/52619 and references therein. Included within the scope of the present invention are also similar peptides known to have specific biological activities such as cell attachment or cell attachment prevention, and which are prepared in analogy with the peptides as mentioned above. In this sense the compound of formula (I) is a RGD-containing peptide, preferably a RGDS-peptide, a GRGDS-peptide, a RGDV-peptide, a RGDE-peptide, and/or a RGDT-peptide, which has been modified to contain at least one alkylphosphonic acid group or a derivative thereof, which is preferably an ester, an amide or a salt thereof.

Preferred compounds of formula (I) are those containing a residue $A_2$ as defined above, preferably a residue of an amino acid or of a sequence of amino acids resp. of a protein or of a polypeptide, preferably a residue of the superfamily of Transforming Growth Factor beta (TGF-β), preferably a Bone Morphogenic Protein (BMP).

The following steps are recommended to be taken for producing the implant according to the present invention, i.e. for treating the surface of the implant with at least one compound of formula (I) above. The implant is first cleaned in a cleaning bath for removing unwanted molecules resp. impurities from the surface. Preferably the implant is first treated with a degreasing agent, for example an organic solvent such as alcohol, chloroform, and another organic solvent and/or an inorganic detergent such as an aqueous alkaline solution based on sodium hydroxide or potassium hydroxide. Subsequently, the implant is carefully rinsed in pure water, preferably in distilled ultra-pure water, having preferably a conductivity resistance of at least 15 Mohm*cm. After cleaning and rinsing, the implant is dried with flowing nitrogen gas or flowing dry or hot air and stored under controlled conditions. Alternatively after degreasing the implant can be further treated in a glow-discharge plasma for cleaning the surface. The clean surface of the implant is then treated with at least one compound of formula (I) or an ester or a salt thereof, i.e. with at least one such compound or a mixture thereof. The compound or the mixture of said compounds is brought onto the surface of the implant by any suitable means, like brushing, spraying, dipping or evaporation, including glow-discharge plasma assisted vapour deposition. The phosphonic acid compound or the ester or the salt thereof is preferably dissolved in a polar solvent, so that a solution with a concentration of from about $1.0\times10^{-5}$ mol/10 ml to $5\times10^{-2}$ mol/10 ml, preferably from about $5\times10^{-4}$ mol/10 ml to $2.0\times10^{-2}$ mol/10 ml with reference to the weight of the solvent is obtained. Preferably the concentration is such that a partial or full (1% to 100%, preferably 50% to 100% of a) monomolecular layer is formed on the implant surface. The preferred solvent is pure distilled water. The implant is left in contact with the solution for a sufficiently long time, preferably for a few minutes up to a few hours. After that the implant is carefully rinsed with pure water and packed with a plastic or metallic clean packaging material preferably into an air tight packaging which preferably is evacuated or filled with an inert gas such as nitrogen or an inert liquid such as pure water as defined herein above. Said pure water may contain inorganic salts, preferably alkali salts, such as alkali chlorides, sulfates, phosphates, phosphonates, preferably the sodium and/or potassium salts, and/or compounds of the formula (I) or an ester or a salt thereof, preferably in a concentration of from about $1.0\times10^{-5}$ mol/10 ml to $5\times10^{-2}$ mol/10 ml, preferably from about $5\times10^{-4}$ mol/10 ml to $2.0\times10^{-2}$ mol/10 ml of solvent, which preferably is distilled water.

Analytical investigations, e.g. X-ray Photoelectron Spectroscopy analysis (XPS) or NMR, have shown that on contacting the phosphonic acid compound of formula (I) with the titanium surface of the implant, immediate adsorption takes place. A strong bond is formed between the surface and the phosphonic acid compound so that a chemical surface modification is obtained. Several different alkane polyphosphonic acids as mentioned herein above were synthesized. Dental implants produced with these compounds according to the present invention have shown excellent results.

The compounds according to the general formula (I), wherein p is 3 to 6, preferably 3 or 4, and n is 4 to 70, preferably 4 to 40, preferably 4 to 22, the salts or esters or amides thereof are new. Examples of such compounds are butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid, heptane-1,4,4,7-tetraphosphonic acid, or nonane-1,5,5,9-tetraphosphonic acid.

The compounds hexaisopropyl butane-1,1,4-triphosphonate and octaisopropyl heptane-1,4,4,7-tetraphosphonate, resp. a mixture of these compounds, are obtained in that an alkalimetal, preferably sodium, tetra lower alkyl methylenediphosphonate, preferably tetraisopropyl methylenediphosphonate, is reacting with at least a stoichiometric amount of a dihalomethane, preferably dibromomethane, in the presence of an organic solvent having no active hydrogen atoms, preferably dry hexane or benzene or toluene.

The reaction is preferably carried out at a temperature within the range of 30° C. to 125° C., preferably 40° C. to 110° C., until the reaction is completed, which generally is within a time period of 10 to 48 hours, preferably 18 to 36 hours.

To the reaction product is then added the purified product of triisopropylphosphite that has been reacted with diisopropyl-3-bromopropane. The obtained mixture of compounds can then be separated in a conventional manner, for example by column chromatography In an analogous way, by reacting 1,4-dibromobutane in excess molar ratio in the range 1:6 to 1:0.5 with triisopropylphosphite, surprisingly the new compounds hexaisopropyl pentane-1,1,5-triphosphonate and octaisopropyl nonane-1,5,5,9-tetraphosphonate are produced. Further, in an analogous way the hexaisopropyl pentane-2,2,5-triphosphonate and hexaisopropyl hexane-2,2,6-triphosphonate were obtained by reacting equal parts of tetraisopropylethane-1,1-diphosphonate with diisopropyl-3-bromopropylphosphonate.

The process is further characterised by that these products are hydrolysed to produce the analogous acids by refluxing them in molar excess of HCl for a time comprised within 1 to 12 hours, preferably 1 to 6 hours. The compounds are then preferably dried under vacuum over $P_2O_5$.

The following Examples illustrate but do not limit the present invention.

EXAMPLE 1

Methylenediphosphonic acid was synthesized according to U.S. Pat. No. 3,400,176 and B. A. Arbusov, Pure Appl. Chem. 9 (1967), pp. 307-353 and references therein. The compound was characterized by NMR ($^1H$, $^{31}P$, $^{13}C$) mass spectroscopic elemental analysis and by its melting point. All these data are in accordance with the literature O. T. Quimby et al., J. of Organomet. Chem. 13, 199-207 (1968).

Propane-1,1,3,3-tetraphosphonic acid was synthesized from tetraisopropyl methylenediphosphonate. The tetraphosphonic acidic solution was concentrated under vacuum, dried over $P_2O_5$ under vacuum. The $^1H$, $^{31}P$ and $^{13}C$ NMR results ($D_2O$) are in accordance with the given literature data.

In an analogous manner propane-1,3-diphosphonic acid, ethane-1,1,2-triphosphonic acid, butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid, heptane-1,4,4,7-tetraphosphonic acid, or nonane-1,5,5,9-tetraphosphonic acid, are synthesized.

EXAMPLE 2

A) A sample made from titanium in the form of a circular plate of 14 mm in diameter, having a thickness of 1 mm, is produced in a conventional manner. The sample surface is provided with a smooth surface roughness by mechanical polishing with diamond paste according to standard procedures. By Atomic force microscopy the surface roughness was measured to a $S_{rms}$ value of ca 6 nm over a surface area of 400 square microns.

B) The implant as produced in chapter A) above is then put into an aqueous solution of (i) methylenediphosphonic acid [$1.5\times10^{-3}$ mol per 10 ml of distilled water], (ii) ethane-1,1,2-triphosphonic acid [$1.2\times10^{-3}$ mol per 10 ml, in distilled water], (iii) propane-1,1,3,3-tetraphosphonic acid [$6.2\times10^{-4}$ mol per 10 ml, in distilled water], (iv) 1-hydroxyethylidene-diphosphonic acid [$1.4\times10^{-3}$ mol per 10 ml, in distilled water] and left there at room temperature for 15 minutes. The implant is then rinsed with pure water and dried.

The implant prepared according to the preparations B(i), B(ii), and B(iii) are plated with rat bone building cells, osteoblasts. The osteogenesis is measured as (I) the cell proliferation and (II) the bone protein synthesis. Comparative test results are given for the untreated implant. The results are given in Table 1. Analogous results are obtained for all the phosphonic acids given herein above both on a smooth and on a rough surface. Analysis with XPS and ToF-SIMS indicated that a molecular (mono) layer was formed on a titanium surface as well as on a $TiO_2$-surface.

TABLE 1

| Preparation | Number of cells* after 4 days (±SEM) | Total protein synthesis* after 8 days (cpm† × $10^4$ per million cells) (±SEM) | Collagen* after 8 days (% of total protein) (±SEM) |
|---|---|---|---|
| B(i) | 36108 (±2485) | 94224 (±8357) | 3.18 (±0.17) |
| B(ii) | 40773 (±1263) | 104503 (±2863) | 3.19 (±0.10) |
| B(iii) | 37290 (±2852) | 92361 (±8237) | 2.30 (±0.29) |
| Comparative Test | 32560 (±2485) | 87842 (±3161) | 2.74 (±0.18) |

*the numbers are given as an average value from three measurements for each test.
†cpm = counts per minute from radio labeled proteins.

The results illustrate the improved osteogenesis of the implants according to the present invention compared to the non treated implants.

EXAMPLE 3

Example 2 is repeated with the difference that the implant is treated with ethane-1,1,3-triphosphonic acid which has been modified by linking the amine terminus of a Glycine molecule to one of the phosphonate groups.

EXAMPLE 4

Examples 2 is repeated with the difference that the implant is treat with ethane-1,1,3-triphosphonic acid which is modified by linking the amine terminus of a GRGDS cell binding polypeptide to one of the phosphonate groups.

EXAMPLE 5

Examples 2 is repeated with the difference that the compound according to formula (I) is ethane-1,1,3-triphosphonic acid which is modified by linking the amine terminus (Methionine) of a human Bone Morphogenic Protein type 2 (BMP-2) to one of the phosphonate groups, which gives analogous test results as given in Table 1.

The invention claimed is:

1. An endosseous implant suitable for application to a human or animal bone, said implant having a surface made from titanium or a titanium alloy, said surface having a smooth or rough texture, wherein said surface has a layer formed thereon of at least one pharmaceutically acceptable organic compound or an ester[, an amide] or a salt thereof, corresponding to the general formula (I):

$$A\text{-}[P(O)(OH)_2]_p \qquad (I),$$

wherein A means $A_1$, and $A_1$ is a residue of a linear, branched or cyclic, saturated or unsaturated, hydrocarbon residue with n carbon atoms, wherein n is a number from 1 to 70, whereby said residue is not interrupted or is interrupted by one or more oxygen and/or nitrogen atoms, wherein each residue $A_1$ carries p phosphonic acid groups, and when n is 1 and p is 2: A is —$CH_2$—, or when n is 1: p is 3 or 4, or when n is 2 to 10: p is 2, provided each phosphonic acid group or phosphonic acid ester group is bound to a different carbon atom within the same molecule; or when n is 2 to 10: p is 3, 4, 5 or 6; or when n is 11 to 70: p is 2, 3, 4, 5 or 6;

or A means $A_2$ and $A_2$ is a residue of an amino acid or of a sequence of amino acids respectively of a protein or of a polypeptide; or a residue of a specific drug molecule, wherein each residue $A_2$ carries p phosphonic acid groups, and p is 1 to 6 when $A_2$ is a residue of an amino acid or of a sequence of amino acids respectively of a protein or of a polypeptide; or p is 1 or 3-6 when $A_2$ is a residue of a specific drug molecule originally not bearing any phosphonate group, optionally falling under the definition given for $A_1$.

2. The implant according to claim 1, wherein $A_1$ is a saturated hydrocarbon residue of the formula —$(C_nH_{2n+2-p})$—, wherein n means 1 to 70.

3. The implant according to claim 1, wherein the pharmaceutically acceptable salt is an alkali salt.

4. The implant according to claim 1, wherein the pharmaceutically acceptable ester is an alkyl phosphonate[, or an ethyl acetate].

5. The implant according to claim 1, wherein the compound of formula (I) is a polyphosphonic acid.

6. The implant according to claim 4, wherein the compound of formula (I) is an ester.

7. The implant according to claim 1, wherein the compound of formula (I) is a Transforming Growth Factor beta (TGF-β) as defined by the members of the superfamily of growth factors, wherein each time the peptide chain has been modified to contain at least one alkylphosphonic acid group or a derivative thereof.

8. The implant according to claim 1, wherein the compound of formula (I) is a Bone Morphogenic Protein (BMP), wherein the peptide chain has been modified to contain at least one alkylphosphonic acid group or a derivative thereof.

9. The implant according to claim 1, wherein the compound of formula (I) is 2-amino-4,4-bis-(diethoxy-phosphoryl)-butyric acid, 2-amino-5-(diethoxy-phosphoryl)-pentanoic acid and/or 2-amino-4-phosphonobutyric acid.

10. The implant according to claim 1, wherein the compound of formula (I) is one of the principal twenty amino acids, wherein the amino acid has been modified to contain at least one alkylphosphonic acid group or a derivative thereof.

11. The implant according to claim 1, wherein the compound of formula (I) is a RGD-containing peptide, which has been modified to contain at least one alkyl-phosphonic acid group or derivative thereof.

12. A process for producing the implant according to claim 1, which comprises treating said surface with at least one organic compound of formula (I) or an ester[, an amide], a salt or a mixture thereof.

13. The implant according to claim 1, in the form of screws, plates, nails, pins or specially formed parts which may be used as prostheses in orthopaedics, for replacing or strengthening broken or diseased bones, in dentistry, for anchoring artificial teeth, or for anchoring of bone anchored hearing prosthesis into the skeletal structure of humans and animals.

14. The implant according to claim 13, wherein said implant is packed with a plastic or metallic packaging material.

15. The implant according to claim 14, wherein said packaging is filled with pure water containing an inorganic salt and/or a compound of the formula (I) or a salt thereof.

16. The implant according to claim 1, wherein n is a number from 1 to 40.

17. The implant according to claim 1, wherein n is a number from 1 to 22.

18. The implant according to claim 1, wherein when n is 1, p is 3.

19. The implant according to claim 1, wherein when n is 2, p is 3, 4 or 5.

20. The implant according to claim 1, wherein when n is 2, p is 3 or 4.

21. The implant according to claim 1, wherein when n is 11 to 70, p is 2, 3, 4 or 5.

22. The implant according to claim 1, wherein when n is 11 to 70, p is 2, 3 or 4.

23. The implant according to claim 1, wherein $A_2$ is a residue of the superfamily of Transforming Growth Factor beta (TGF-β).

24. The implant according to claim 1, wherein p is 1, 2, 3 or 4 when $A_2$ is a residue of an amino acid or of a sequence of amino acids respectively of a protein or a polypeptide.

25. The implant according to claim 1, wherein p is 1, 2 or 3 when $A_2$ is a residue of an amino acid or of a sequence of amino acids respectively of a protein or a polypeptide.

26. The implant according to claim 1, wherein p is 1 when $A_2$ is a residue of a specific drug molecule originally not bearing any phosphonate group, optionally falling under the definition given for $A_1$.

27. The implant according to claim 2, wherein n is 1 to 40.

28. The implant according to claim 2, wherein n is 1 to 22.

29. The implant according to claim 3, wherein the salt is a sodium or potassium salt.

30. The implant according to claim 5, wherein the polyphosphonic acid is selected from the group consisting of methylenediphosphonic acid, ethane-1,2-diphosphonic acid, propane-1,3-diphosphonic acid, [propane-1,3-diphosphonic acid,] ethane-1,1,2-triphosphonic acid, butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid, heptane-1,4,4,7-tetraphosphonic acid, propane-1,1,3,3-tetraphosphonic acid, [nonane-1,5,5,9-tetraphosphonic acid,] an ester thereof, a salt thereof, and a mixture thereof.

31. The implant according to claim 6, wherein the ester is selected from the group consisting of tetra isopropyl methylenediphosphonate, hexaethyl ethane-1,1,2-triphosphonate, hexaisopropyl butane-1,1,4-triphosphonate, hexaisopropyl pentane-1,1,5-triphosphonate, hexaisopropyl pentane-2,2,5-triphosphonate, hexaisopropyl hexane-2,2,6-triphosphonate, octaisopropyl propane-1,1,3,3-tetraphosphonate[,] *and* octaisopropyl heptane-1,4,4,7-tetraphosphonate [and octaisopropyl nonane-1,5,5,9-tetraphosphonate].

32. The implant according to claim 7, wherein the compound of formula (I) is a Transforming Growth Factor beta (TGF-β) as defined by the members of the superfamily of growth factors, selected from the group consisting of TGF-β1, TGF-β2, TGF-β3, TGF-β4 and TGF-β5, wherein each time the peptide chain has been modified to contain at least one alkylphosphonic acid group or an ester[, an amide] or a salt thereof.

33. The implant according to claim 8, wherein the compound of formula (I) is a Bone Morphogenic Protein (BMP), selected from the group consisting of BMP-2 (BMP-2a), BMP-3, BMP-4 (BMP-2b), BMP-5, BMP-6, BMP-7 (OP-1), BMP-8 (OP-2), BMP-9, BMP-10, BMP-11, BMP-12 and BMP-13, wherein the peptide chain has been modified to contain at least one alkylphosphonic acid group or an ester[, an amide] or a salt thereof.

34. The implant according to claim 10, wherein the compound of formula (I) is selected from the group consisting of arginine, glycine, aspartic acid, alanine, valine, proline, serine, threonine, cysteine and lysine, wherein the amino acid has been modified to contain at least one alkylphosphonic acid group or an ester[, an amide] or a salt thereof.

35. The implant according to claim 11, wherein the compound of formula (I) is selected from the group consisting of a RGDS-peptide, a GRGDS-peptide, a RGDV-peptide, a RGDE-peptide, a RGDT-peptide, and a mixture thereof, which has been modified to contain at least one alkyl-phosphonic acid group or an ester[, an amide] or a salt thereof.

36. The implant according to claim 14, wherein said implant is packed with a plastic or metallic packaging material, into an air tight packaging which is evacuated or filled with an inert gas or an inert liquid.

37. The implant according to claim 36, wherein said air tight packaging is filled with pure water containing an inorganic alkali salt and/or a compound of the formula (I) or a salt thereof in a concentration of from about $1.0\times10^{-5}$ mol/10 ml to $5\times10^{-2}$ mol/10 ml, of the water.

38. The implant according to claim 36, wherein said air tight packaging is filled with pure water containing an inorganic alkali salt and/or a compound of the formula (I) or a salt thereof in a concentration of from about $5\times10^{-4}$ mol/10 ml to $2.0\times10^{-2}$ mol/10 ml of the water.

* * * * *